US011110051B2

(12) United States Patent
Randhawa et al.

(10) Patent No.: US 11,110,051 B2
(45) Date of Patent: Sep. 7, 2021

(54) **TOPICAL COMPOSITIONS COMPRISING *PICHIA ANOMALA* AND N-ACETYL GLUCOSAMINE**

(71) Applicant: Johnson & Johnson Consumer Inc., Skillman, NJ (US)

(72) Inventors: Manpreet Randhawa, Robbinsville, NJ (US); Marisa DeVita Dufort, Hillsborough, NJ (US); Peter Konish, Easton, PA (US); Prithwiraj Maitra, Hillsborough, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/266,694

(22) Filed: Feb. 4, 2019

(65) Prior Publication Data
US 2020/0069564 A1 Mar. 5, 2020

Related U.S. Application Data

(60) Provisional application No. 62/724,820, filed on Aug. 30, 2018.

(51) Int. Cl.
| | | |
|---|---|---|
| *A61K 8/9728* | (2017.01) |
| *A61K 8/60* | (2006.01) |
| *A61K 9/00* | (2006.01) |
| *A61Q 19/00* | (2006.01) |
| *A61Q 19/08* | (2006.01) |
| *C12R 1/84* | (2006.01) |
| *A61K 8/92* | (2006.01) |
| *A61K 31/7008* | (2006.01) |
| *A61K 36/064* | (2006.01) |
| *A61Q 17/00* | (2006.01) |
| *A61P 17/00* | (2006.01) |
| *A61P 17/18* | (2006.01) |
| *A61C 17/00* | (2006.01) |
| *C12N 1/16* | (2006.01) |

(52) U.S. Cl.
CPC ............. *A61K 8/9728* (2017.08); *A61K 8/60* (2013.01); *A61K 9/0014* (2013.01); *A61Q 19/007* (2013.01); *A61Q 19/08* (2013.01); *A61C 17/00* (2013.01); *A61K 8/92* (2013.01); *A61K 31/7008* (2013.01); *A61K 36/064* (2013.01); *A61P 17/00* (2018.01); *A61P 17/18* (2018.01); *A61Q 19/00* (2013.01); *C12N 1/165* (2021.05); *C12R 2001/84* (2021.05); *Y10S 435/938* (2013.01)

(58) Field of Classification Search
CPC ...... A61Q 19/00; A61Q 19/007; A61Q 19/08; A61Q 9/0014; A61Q 17/00; A61K 8/9728; A61K 8/60; A61K 9/0014; A61K 9/00; A61K 8/92; A61K 36/064; A61K 31/7008; Y10S 435/938; C12R 1/84; A61P 17/00; A61P 17/18
See application file for complete search history.

(56) References Cited

U.S. PATENT DOCUMENTS

| | | | |
|---|---|---|---|
| 4,691,820 A | 9/1987 | Martinez | |
| 4,992,264 A | 2/1991 | Diot et al. | |
| 5,467,868 A | 11/1995 | Abrams et al. | |
| 5,488,815 A | 2/1996 | Abrams et al. | |
| 5,577,367 A | 11/1996 | Abrams et al. | |
| 5,696,686 A | 12/1997 | Sanka et al. | |
| 5,704,468 A | 1/1998 | Lust et al. | |
| 5,823,327 A | 10/1998 | Wu et al. | |
| 6,018,931 A | 2/2000 | Byram et al. | |
| 6,050,398 A | 4/2000 | Wilde et al. | |
| D435,966 S | 1/2001 | Duis et al. | |
| 6,620,420 B2 | 9/2003 | Lanzendörfer et al. | |
| 7,192,615 B2 | 3/2007 | Liu et al. | |
| 7,419,688 B2 | 9/2008 | Perrier et al. | |
| RE41,339 E | 5/2010 | Yu et al. | |
| 8,158,111 B2 * | 4/2012 | Roberto ................... A61K 8/37 424/59 |
| 8,378,090 B2 | 2/2013 | Petiard et al. | |
| 8,496,976 B2 | 7/2013 | Gore et al. | |
| 8,628,783 B2 | 1/2014 | Iino et al. | |
| 8,652,532 B2 | 2/2014 | Courtois et al. | |
| 8,828,412 B2 | 9/2014 | Yu et al. | |
| 9,480,645 B2 | 11/2016 | Yu | |
| 2003/0165545 A1 | 9/2003 | Huth et al. | |
| 2005/0226834 A1 | 10/2005 | Lambino et al. | |
| 2006/0141014 A1 | 6/2006 | Eknoian et al. | |
| 2007/0092469 A1 | 4/2007 | Jacobs | |
| 2007/0141018 A1 | 6/2007 | Courtois Didier et al. | |
| 2007/0196523 A1 | 8/2007 | Koganov | |
| 2009/0241242 A1 | 10/2009 | Beatty et al. | |
| 2013/0237496 A1 | 9/2013 | Paufique | |
| 2017/0172913 A1 | 6/2017 | Ballesteros et al. | |
| 2018/0036225 A1 | 2/2018 | Figueroa et al. | |
| 2018/0036233 A1 | 2/2018 | Shabaik et al. | |
| 2018/0161267 A1 | 6/2018 | Randhawa | |
| 2019/0008910 A1 | 1/2019 | Liu-Walsh et al. | |

FOREIGN PATENT DOCUMENTS

| | | |
|---|---|---|
| CN | 106619976 A | 5/2017 |
| DE | 102009045753 A | 4/2011 |

(Continued)

OTHER PUBLICATIONS

U.S. Appl. No. 62/724,807, filed Aug. 30, 2018, Johnson & Johnson Consumer Inc.
U.S. Appl. No. 62/724,812, filed Aug. 30, 2018, Johnson & Johnson Consumer Inc.
U.S. Appl. No. 62/724,820, filed Aug. 30, 2018, Johnson & Johnson Consumer Inc.
U.S. Appl. No. 62/432,945, filed Dec. 12, 2016, Johnson & Johnson Consumer Inc.

(Continued)

*Primary Examiner* — Sean C. Barron

(57) ABSTRACT

The present invention provides a topical composition comprising an extract of *Pichia anomala* and n-acetyl glucosamine.

13 Claims, No Drawings

(56) References Cited

FOREIGN PATENT DOCUMENTS

| EP | 1639994 A2 | 3/2006 |
|---|---|---|
| EP | 1707191 B | 10/2006 |
| EP | 1962875 A | 5/2007 |
| EP | 2277502 A | 1/2011 |
| EP | 2662072 A | 11/2013 |
| EP | 3165257 A | 5/2017 |
| EP | 3181142 A | 6/2017 |
| FR | 2626469 A | 8/1989 |
| FR | 2897266 A | 8/2007 |
| FR | 2906719 A | 4/2008 |
| FR | 2938768 A | 5/2010 |
| FR | 2938768 A | 2/2011 |
| FR | 2976490 A | 7/2013 |
| FR | 3016521 A | 7/2015 |
| JP | A-62-212317 | 9/1987 |
| JP | S62 234011 A | 10/1987 |
| JP | 2001181160 A | 7/2001 |
| WO | WO 02/102399 A2 | 12/2002 |
| WO | WO 2007/053271 A | 5/2007 |
| WO | WO 2012/175868 A | 12/2012 |
| WO | WO 2013/178965 A | 12/2013 |
| WO | WO 2019/123417 | 6/2019 |
| WO | WO 2020/021481 A | 1/2020 |

OTHER PUBLICATIONS

U.S. Appl. No. 15/799,350, filed Oct. 31, 2017, 2018/0161267, Jun. 14, 2018, Johnson & Johnson Consumer Inc.
U.S. Appl. No. 16/117,434, filed Aug. 30, 2018, 2019/0008910, Jan. 10, 2019, Johnson & Johnson Consumer Inc.
U.S. Appl. No. 62/268,618, filed Dec. 17, 2015, Johnson & Johnson Consumer Inc.
U.S. Appl. No. 15/375,365, filed Dec. 17, 2016, 2017/0172913, Jun. 22, 2017 Johnson & Johnson Consumer Inc.
Ando et al., "Quasi-Drugs Developed in Japan for the Prevention or Treatment of Hyperpigmentary Disorders", *International Journal of Molecular Sciences* (2010) 11:2566-2575.
Anonymous, "Olivem 1000", Nov. 2, 2002, retrieved from the internet, URL:https://www.lotioncrafter.com/reference/Olivem_1000.pdf [retrieved on Feb. 6, 2011] (XP055448618).
Baviera et al., "Microbiota in Healthy Skin and in Atopic Eczema", *BioMed Research International* (2014), vol. 2014, pp. 1-6, DOI 10.1155/2014/436921.
De Guertechin, "Classification of Surfactants", Handbook of Cosmetic Science and Technology, eds. A. Barel, M. Paye and H. Maibach and published by Marcel Dekker, Inc. New York, NY, Chapter 37, pp. 431-450, (2001).
O'Goshi, "Suction Chamber Method for Measurement of Skin Mechanics: The Cutometer", Handbook of Non-Invasive Methods and the Skin, 2nd Edition, eds. J. Serup, G. Jemec & G. Grove, Chapter 66 (2006) pp. 579-582.
Henry et al, "Synthesis of a molecularly imprinted polymer to isolate glucosamine from plant extracts by an ionic-non-covalent dual approach", *International Journal of Cosmetic Science*, 2015, 37, 196-206.
Luciano Polonellirodolfo Lorenziniflavia De Bernardsigiulia Morace: "Potential therapeutic effect of yeast killer toxin", Mycopathologia, Kluwer Academic Publishers, XX, vol. 96, No. 2, (Nov. 1, 1986), pp. 103-107, XP009193593.
Mintel Database GNPD [Online], "Anti-aging neck cream", Nov. 2011 (XP002777989).
Mintel Database GNPD [Online], "Gel cream", Nov. 2015 (XP002777990).
Mintel Database GNPD [Online], "Twinkle twinkle facial lotion", Feb. 2013 (XP002777991).
Miyazaki et al., "Genistein and daidzein stimulate hyaluronic acid production in transformed human keratinocyte culture and hairless mouse skin", *Skin Pharmacology and Applied Skin Physiology*(2002) 15(3):175-183.

Sirtuin Support Facial Contour Lifting Serum, Skinn Cosmetics, Sep. 2010.
Sharpell and Manowitz, Chapter 51 "Preservation of Cosmetics", pp. 887-900, Disinfection, Sterilization, and Preservation, Fourth Edition, ed. Seymour S. Block, Part VII Antimicrobial Preservatives and Protectants, published by Lea & Febiger, Philadelphia, PA (1991).
Solano et al., "Hypopigmenting agents: an updated review on biological, chemical and clinical aspects", *Pigment Cell Res.* (2006) 19:550-571.
Street R.A. et al.: "Cichorium intybus: Traditional uses, phytochemistry, pharmacology, and toxicology", *Evidence-Based Complementary and Alternative Medicine* 2013 Oxford University Press GBR, vol. 2013, 2013, XP55160986.
UGL Complex, Barnet Products Corporation, Apr. 8, 2010.
Zocchi, Skin Feel Agents, Handbook of Cosmetic Science and Technology, eds. A. Barel, M. Paye and H. Maibach and published by Marcel Dekker, Inc. New York, NY, Chapter 35, pp. 399-415, (2001).
European Search Report dated Dec. 19, 2017, for EP Application No. 19194767.0
European Search Report dated Dec. 19, 2017, for EP Application No. 19194766.2.0.
European Search Report dated Dec. 19, 2017, for EP Application No. 19194773.8.
Mintel Database GNPD [Online], "Face Lift SPF 20" Sep. 2011 (XP055648134.
Li Wen-Hwa et al: "Topical stabilized retinol treatment induces the expression of HAS genes and HA production in human skin in vitro and in vivo", Archives of Dermatological Research, Springer, International, Berlin, DE.
Craig, J.P. et al. TFOS Dews II definition and classification report. *Ocul Surf.* 2017; 15: 256-283.
Dai, et al., 2013 (Liposomes containing bile salts as novel ocular delivery systems for tacrolimus (FK506): in vitro characterization and improved corneal permeation, International Journal of Nanomedicine 2013:8 1921-1933). (Year: 2013).
David A. Leigh et al Angew. Chem Int. Ed., 2001, 40, No. 8, pp. 1538-1542.
Douglass, et al. 2018 (Population genomics shows no distinction between pathogenic Candida krusei and environmental Pichia kudriavzevii: Once species, four names, PLoS Pathog 14(7): e 1007138; https://doi.org/10.1371/journal.ppat.1007138 (Year: 2018).
Dreyfuss JL, Regatieri CV, Coelho B, et al. Altered hyaluronic acid content in tear fluid of patients with adrenoviral conjunctivitis. An Acad Bras Cienc. 2015;87(1):455-462.
Eric Carlson, et al., "Impact of Hyaluronic Acid-Containing Artificial Tear Products on Reepithelialization in an In Vivo Corneal Wound Model", Journal of Ocular Pharmacology and Therapies, vol. 34, No. 4, pp. 360-364, May 1, 2018.
International Search Reports dated Nov. 28, 2019 PCT/IB2019/056345 and PCT/IB2019/056341 dated Nov. 29, 2019.
Jean-Claude Chambron et al. Pure & Appl. Chem., 1990, vol. 62, No. 6, pp. 1027-1034.
Kurtzman, et al. 2008 (Phylogenetic relationships among species of Pichia, Issatchenkia and Williopsis determined from multigene sequence analysis, and the proposal of Barnettozyma gen.nov., Lindnera gen.nov. and Wickerhamomyces gen.nov.FEMS Yeast Res 8 (2008) 939-954) (Year: 2008).
Laemmli UK. 1970., Cleavage of structual proteins during the assembly of the head of bacteriophage T4. Nature 227: 680-685.
Maker AV, Katabi N, Gonen M, et al. Pancreatic cyst fluid and serum mucin levels predict dysplasia in intraductal papillary mucinous neoplasms of the pancreas. *Ann Surg Oncol.* 2011;18(1):199-206.
Martins Jr, Passerotti CC, Maciel RM, Sampaio Lo, Dietrich CP and Nader HB. 2003., Practical determination of hyaluronan by a new noncompetitive fluorescence-based assay on serum of normal and cirrhotic patients. Anal Biochem 319: 65-72.
Pacella, E., Pascella, F., De Paolis, G., et al. *Glycosaminoglycans in the human cornea: age-related changes.* Ophthalmol. Eye Dis. 7:1-5, 2015).
U.S. Appl. 60/783,557, filed on, Mar. 17, 2006.

(56) References Cited

OTHER PUBLICATIONS

Uchino Y, Uchino M, Yokoi N, et al. Altercation of Tear Mucin 5AC in Office Workers Using Visual Display Terminals: The Osaka Study. *JAMA Ophthalmol.* n2014;132(8):985-992.

European search report dated Feb. 20, 2018, for EP application 17206433.9.

Frenkel ES, Ribbeck K, "Salivary mucins in host defense and disease prevention," J Oral Microbiol., 2015; 7: 29759.

Kashyap B, Kullaa AM., Regulation of mucin 1 expression and its relationship with oral disease, Archives of Oral Biology, 117: 104791; 2020.

Chang, W.I., Chang, J.Y., Kim, Y.Y., Leeb, G., & Kho, H.S. MUC1 expression in the oral mucosal epithelial cells of the elderly, Archives of Oral Biology, 2011; 56, 885-890.

Sengupta A., Valdramidou, D., Huntly, S., Distribution of MUC1 in the normal human oral cavity is localized to ducts of minor salivary glands, Arch Oral Biol., 2001; 46: 529-38.

Pramanik, R., Osailan, S.M., Challacomb, S.J., et al., Protein and mucin retention on oral mucosal surfaces in dry mouth patients, Eur J Oral Sci, 2010; 118: 245-53.

Akira, S., & Takeda, K., Toll-like receptor signalling. Nature Reviews Immunology, 2004; 4(7), 449-511.

Ueno, K., Koga, T., Kato, K., Golenback, D.T., Gendler, S. J., Kai, H., & Kim, K.C. MUC1 mucin is a negaitve regulator of toll-like receptor signalling. American Journal of Respiratory Cell and Molecular Biology. 2008; 38, 263-268.

*Annual review of selected scientific literature: A report of the Committee on Scientific Investigation of the American Academy of Restorative Dentistry.* Journal of Prosthetic Dentistry 2008 (Dec.) pp. 816-877.

Lundmark A, Johannsen G, Eriksson K, Kats A, Jansson L, Tervahartiala T, et al., *Mucin 4 and matrix metalloproteinase 7 as novel salivary biomarkers for periodontitis.* J Clin Periodontal 2017; 44:247-54.

U.S. Appl. No. 62/724,807, filed Aug. 30, 2018, JJCI.
U.S. Appl. No. 16/266,607, filed Feb. 4, 2019, Publ. No. 2020-0069562, Mar. 5, 2020, JJCI (Abandoned).
U.S. Appl. No. 62/724,812, filed Aug. 30, 2018, JJCI.
U.S. Appl. No. 16/266,645, filed Feb. 4, 2019, Publ. No. 2020-0069563, Mar. 5, 2020, JJCI.
U.S. Appl. No. 62/724,820, Aug. 30, 2018, JJCI.
U.S. Appl. No. 16/266,694, filed Feb. 4, 2019, Publ. No. 2020-0069564, Mar. 5, 2020, JJCI.
U.S. Appl. No. 62/432,945, filed Dec. 12, 2016, JJCI.
U.S. Appl. No. 15/799,350, filed Oct. 31, 2017, Publ. No. 2018/0161267, Jun. 14, 2018, JJCI (Granted-10,206,870).
U.S. Appl. 16/117,434, filed Aug. 30, 2018, Publ. No. 2019/0172913, Jun. 22, 2017, JJCI (Granted-10,543,240).
U.S. Appl. No. 62/268,618, filed Dec. 17, 2015, JJCI.
U.S. Appl. No. 15/375,365, filed Dec. 17, 2016, Publ. No. 2017/0172913, Jun. 22, 2017, JJCI (Abandoned).
U.S. Appl. No. 62/703,941, filed Jul. 27, 2018, JJSVI.
U.S. Appl. No. 16/519,149, filed Jul. 23, 2019, JJSVI.
U.S. Appl. No. 62/703,948, filed Jul. 27, 2018, JJSVI.
U.S. Appl. No. 16/519,161, filed Jul. 23, 2019, JJSVI (Abandoned).
U.S. 17/029,236, filed Sep. 23, 2020, JJSVI.
U.S. Appl. No. 62/877,395, filed Jul. 23, 2019, JJCI.
U.S. Appl. No. 16/933,512, filed Jul. 20, 2020, JJCI.
Bowen, P.; "Particle Size Distribution Measurement from Millimeters to Nanometers and from Rods to Platelets," Journal of Dispersion Science and Technology, Taylor and Francis Group, NY; vol. 23, No. 5, Jan. 1, 2002; pp. 631-662.
Extended European Search Report, Appln. No. 20208692.2-1112, dated Mar. 16, 2021.

\* cited by examiner

TOPICAL COMPOSITIONS COMPRISING *PICHIA ANOMALA* AND N-ACETYL GLUCOSAMINE

CROSS-REFERENCE TO RELATED APPLICATIONS

This application claims the benefit of U.S. provisional application 62/724,820 filed on Aug. 30, 2018, the complete disclosure of which is hereby incorporated herein by reference for all purposes.

FIELD OF THE INVENTION

The present invention provides a method of treating skin by topically applying to skin a combination of an extract of *Pichia anomala* and n-acetyl glucosamine. Additionally, a topical composition comprising a combination of an extract of *Pichia anomala* and n-acetyl glucosamine is provided.

BACKGROUND OF THE INVENTION

Hyaluronic acid is found in skin at the periphery of collagen and elastin fibers and where these fibers intersect. Hyaluronic acid is localized not only in the dermis but also in the epidermal intercellular spaces, especially the middle spinous layer, but not in the stratum corneum (SC) or stratum granulosum. In aged skin, the level of hyaluronic acid decreases and it disassociates from collagen and elastin. Skin containing reduced levels of hyaluronic acid also demonstrates reduced water binding, which may be involved in the changes noted in aged skin, including wrinkling, altered elasticity, reduced turgidity and diminished capacity to support the microvasculature of the skin. As one of the primary glycosaminoglycans (GAGs), hyaluronic acid can bind 1000 times its weight in water, and may help the skin retain and maintain water. It is found in all connective tissue and is produced mainly by fibroblasts and keratinocytes in the skin.

Different methods have been proposed for combating wrinkles and fine lines, including injection of hyaluronic acid. Injection of exogenous hyaluronic acid is used as a temporary dermal filling agent in soft tissue augmentation procedures. However, injected hyaluronic acid has a limited lifetime. On the other hand, penetration of exogenous hyaluronic acid into the skin has proved difficult to accomplish by topical application.

*Pichia* is a genus of yeasts in the family Saccharomycetaceae. More than 100 species of this genus are known. The most well-known species include *Pichia anomala*, *Pichia guilliermondii*, *Pichia norvegensis*, and *Pichia ohmeri*.

*Pichia anomala* (formerly named *Hansenula anomala*) can be found in raw milk and cheese. The extracts of yeasts of the genus *Pichia* are rich in mannans, polysaccharides composed of mannose monomers. *Pichia anomala* and mannans are known to be used in the treatment of aging skin. See, for example, FR 2938768, FR 2906719, FR 2897266 and FR 2976490.

PRO-LIPISKIN® is a commercially available cosmetic ingredient containing extract of *Pichia anomala*. It is produced by a *Pichia* strain isolated from sugar cane. It is available from Silab-France.

US 2017/0172913A1 relates to topical compositions comprising combinations of *Pichia anomala* extract and chicory root extract that provide increased production of hyaluronic acid, along with methods of treating signs of skin aging and improving skin barrier protection and skin moisturization.

N-acetyl glucosamine is a sugar amine and building block for GAGs. It is used in a number of cosmetic skin care products, such as NEOSTRATA Skin Active Retinol+NAG Complex commercially available from NeoStrata Company Inc.

U.S. Pat. No. RE41339 discloses a variety of n-acetyl aldosamines, n-acetylamino acids, and other n-acetyl compounds, including n-acetyl glucosamine, for topical use on skin, nails, and hair. The compounds provide multiple anti-aging benefits, such as alleviating thinning skin, fragile skin, fine lines, wrinkles, and so forth.

*Pichia anomala* extract and n-acetyl glucosamine work through different biological mechanisms and result in improvement of different clinical benefits. N-acetyl glucosamine is known as one of the substrate required for HA production. *Pichia anomala* extract works through a hydration pathway by increasing the activity of Hyaluronic Acid Synthase 2 enzyme that translates to the clinical benefits including hydration, improved skin barrier, firming, etc.

Although the art provides topical uses for extracts of *Pichia anomala* and n-acetyl glucosamine separately, applicants have now discovered that topical application of a combination of these two ingredients at relatively low amounts still unexpectedly provides excellent activity for producing hyaluronic acid. This provides significant benefits for skin, including improving, reducing, inhibiting, or delaying the appearance of at least one sign of aging in skin, and enhancing skin barrier protection and skin moisturization, using cost effective amounts of actives, especially the extract of *Pichia anomala*. Accordingly, new methods of treating signs of skin aging, for example, are now available.

SUMMARY OF THE INVENTION

The present invention relates to a topical composition comprising an extract of *Pichia anomala* and n-acetyl glucosamine.

The invention also relates to a topical composition comprising about 0.052 weight percent of an extract of *Pichia anomala* and about 2 weight percent of n-acetyl glucosamine.

The invention also relates to a method of treating a sign of skin aging, comprising topically applying to skin in need of treatment for skin aging a topical composition comprising an extract of *Pichia anomala* and n-acetyl glucosamine.

The invention further provides a method of improving skin barrier function and moisturization, comprising topically applying to skin in need of improving skin barrier function and moisturization a topical composition comprising an extract of *Pichia anomala* and n-acetyl glucosamine.

The invention also provides a method of increasing the amount of hyaluronic acid produced by skin when contacted with an extract of *Pichia anomala*, comprising contacting the skin with a composition comprising the extract of *Pichia anomala* and n-acetyl glucosamine.

DETAILED DESCRIPTION

The topical composition of the present invention improves the production of hyaluronic acid in the skin by synergistic action of extracts of *Pichia anomala* and n-acetyl glucosamine.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, percentages used to express amounts of ingredients are percentage by weight (i.e., % (W/W). Similarly, weight ratios used to express relative proportions of ingredients are also determined using percentage by weight (i.e., weight ratios are calculated by dividing the percentage by weight of one ingredient by another). Unless stated otherwise, all ranges are inclusive of the endpoints, e.g., "from 4 to 9" includes the endpoints 4 and 9.

As used herein, a "product" is optionally in finished packaged form. In one embodiment, the package is a container such as a plastic, metal or glass tube or jar containing the composition. The product may further contain additional packaging such as a plastic or cardboard box for storing such container. In one embodiment, the product comprises a composition of the invention and contains instructions directing the user to apply the composition to the skin or hair.

As used herein, "topically applying" means directly laying on or spreading on outer skin, the scalp, or hair, e.g., by use of the hands or an applicator such as a wipe, roller, or spray.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically acceptable" means that the ingredients the term describes are suitable for use in contact with tissues (e.g., the skin or hair) without undue toxicity, incompatibility, instability, irritation, allergic response, or the like.

In certain embodiments, the compositions of the present invention are suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "treating signs of skin aging" refers to mitigating, reducing, preventing, improving, or eliminating the presence or signs of skin aging described above.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "improving the firmness of skin" means the enhancing of the firmness or elasticity of the skin, preventing the loss of firmness or elasticity of skin, or preventing or treating sagging, lax and loose skin. The firmness or elasticity of the skin can be measured by use of a cutometer. See Handbook Of Non-Invasive Methods And The Skin, eds. J. Serup, G. Jemec & G. Grove, Chapter 66.1 (2006). The loss of skin elasticity or firmness may be a result of a number of factors, including but not limited to aging, environmental damage, or the result of an application of a cosmetic to the skin.

As used herein, "improving the texture of skin" means the smoothing of the surface of the skin to remove either bumps or crevasses on the skin surface.

As used herein, "improving the appearance of wrinkles in skin" means preventing, retarding, arresting, or reversing the process of wrinkle and fine line formation in skin.

As used herein, the term "safe and effective amount" means an amount sufficient to induce the desired effect, but low enough to avoid serious side effects. The safe and effective amount of the compound, extract, or composition will vary with, e.g., the age, health and environmental exposure of the end user, the duration and nature of the treatment, the specific extract, ingredient, or composition employed, the particular carrier utilized, and like factors.

As used herein, "skin in need of improving skin barrier function and moisturization" means skin that is, but not limited to, lacking in moisture, lacking in sebum, cracked, dry, itchy, scaly, xerodermic, dehydrated, lacks suppleness, lacks radiance, dull, or lacks lipids.

As described herein, applicants have discovered that topical application of a combination of low levels of an extract of *Pichia anomala* and n-acetyl glucosamine provides unexpectedly good skin barrier function, skin moisturization, and skin anti-aging benefits.

Applicants have also discovered that topical application of a composition containing a combination of an extract of *Pichia anomala* and n-acetyl glucosamine enhances the endogenous hyaluronic acid ("HA") level in skin above the level achieved using only the extract of *Pichia anomala*, even at a higher amount. Topical use of such a composition can increase the levels of hyaluronic acid to a direction found in younger skin thereby providing the structural support to skin to reduce the appearance of signs of aging in skin.

*Pichia anomala*

The topical composition comprises one or more extracts of *Pichia anomala*. In particular, such extracts may be extracts produced using one of the various strains of *Pichia anomala* isolated from the fruit or other aerial parts of a plant. Any cosmetically acceptable extract of *Pichia anomala* may be used.

One example of a suitable extract of *Pichia anomala* is PRO-LIPISKIN, commercially available from Silab-France. It is produced from a strain of *Pichia anomala* present on sugar cane.

Another example of a suitable extract of *Pichia anomala* is produced from a strain of *Pichia anomala* present on fruit or leaves of Kiwi plant.

The extract of *Pichia anomala* may be provided as a solution containing dry matter (the extract) in the range of about 20 wt %, more specifically 2 to 10 wt %, most specifically 3 to 7 wt %.

Solvents for such solutions include water, alcohols, glycols and the like. In one embodiment, the solvent is at least about 90 wt % water, or at least about 95 wt % water.

N-Acetyl Glucosamine

The topical composition also contains n-acetyl glucosamine. N-acetyl glucosamine has the structure:

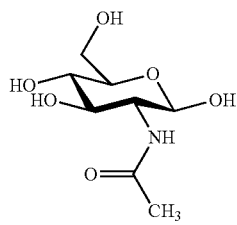

Amounts

Any suitable amounts of *Pichia anomala* extract and n-acetyl glucosamine may be used in the compositions of the present invention. Preferably, the compositions comprise safe and effective amounts of both ingredients. In particular, the amounts of *Pichia anomala* extract and n-acetyl glucosamine used are cosmetically acceptable and are selected to achieve the desired treatment of skin for a particular condition, such as signs of aging, decreased barrier function, or decreased moisturization.

In certain preferred embodiments, the compositions comprise from about 0.01 to about 1% by weight of *Pichia anomala* extract, more preferably about 0.025 to about 0.25% by weight of *Pichia anomala* extract. In one embodiment, the composition comprises about 0.052% by weight of *Pichia anomala* extract.

In certain preferred embodiments, the compositions comprise from about 0.01 to about 10% by weight, more preferably about 0.5 to about 5% by weight, of n-acetyl glucosamine. In one embodiment, the composition comprises about 2% by weight of n-acetyl glucosamine.

In certain embodiments, the weight ratio of *Pichia anomala* extract to n-acetyl glucosamine in the compositions is from about 0.01 to about 0.05. In one embodiment, the weight ratio of *Pichia anomala* extract to n-acetyl glucosamine in the compositions is about 0.026.

Topical Compositions

The compositions of the present invention are applied topically to human skin or hair. Accordingly, the composition may further include a cosmetically acceptable topical carrier that may be from about 50% to about 99.99%, by weight, of the composition (e.g., from about 80% to about 99%, by weight, of the composition). In a preferred embodiment of the invention, the cosmetically acceptable topical carrier includes water.

The compositions may be made into a wide variety of product types that include but are not limited to lotions, creams, gels, sticks, sprays, ointments, cleansing liquid washes and solid bars, shampoos and hair conditioners, hair fixers, pastes, foams, powders, mousses, shaving creams, wipes, patches, hydrogels, film-forming products, facial masks and skin masks, films and make-up such as foundations, and mascaras. These product types may contain several types of cosmetically acceptable topical carriers including, but not limited to solutions, suspensions, emulsions such as microemulsions and nanoemulsions, gels, solids and liposomes. The following are non-limiting examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include propylene glycol, polyethylene glycol, polypropylene glycol, glycerol, 1,2,4-butanetriol, sorbitol esters, 1,2,6-hexanetriol, ethanol, and mixtures thereof.

Compositions useful in the subject invention may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include those known in the art. Examples of particularly suitable emollients include vegetable oils, mineral oils, fatty esters, and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

The composition of the present invention may include water or alternatively be anhydrous or be an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening agent(s).

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of emulsifiers are well known in the art.

Lotions and creams can be formulated as emulsions. Typically, such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contain between about 0.1% and 5%, by weight, of such gelling agents.

In one embodiment, the composition is a gel cream. The gel cream aesthetic is characterized with a watery break, semi-translucent aspect and light after-feel. As used herein, the term "gel cream" means a formulation with low levels of oil droplets suspended in aqueous gel matrix.

The compositions of the present invention can also be formulated into a solid formulation (e.g., a wax-based stick, soap bar composition, powder, or a wipe containing powder).

The compositions may contain, in addition to the components above, a wide variety of additional oil-soluble materials and/or water-soluble materials conventionally used in compositions for use on skin and hair, at their art-established levels.

Additional Cosmetically Active Agents

The compositions of the present invention may further comprise any of a variety of additional cosmetically active agents. Examples of suitable additional active agents include: skin lightening agents, darkening agents, additional anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, antiperspiration agents, astringents, deodorants, hair removers, hair growth enhancing agents, hair growth delaying agents, firming agents, hydration boosters, efficacy boosters, anti-callous agents, agents for skin conditioning, anti-cellulite agents, odor-control agents such as odor masking or pH-changing agents, and the like.

Examples of various suitable additional cosmetically acceptable actives include hydroxy acids; benzoyl peroxide; D-panthenol; UV filters such as but not limited to avobenzone (PARSOL 1789), bisdisulizole disodium (NEO HELIOPAN AP), diethylamino hydroxybenzoyl hexyl benzoate (UVINUL A Plus), ecamsule (MEXORYL SX), methyl anthranilate, 4-aminobenzoic acid (PABA), cinoxate, ethylhexyl triazone (UVINULT 150), homosalate, 4-methylbenzylidene camphor (PARSOL 5000), octyl methoxycinnamate (Octinoxate), octyl salicylate (Octisalate), padimate O (ESCALOL 507), phenylbenzimidazole sulfonic acid (ENSULIZOLE), polysilicone-15 (PARSOL SLX), trolamine salicylate, Bemotrizinol (TINOSORB S), benzophenones 1-12, dioxybenzone, drometrizole trisiloxane (MEXORYL XL), isotrizinol (UVASORB HEB), octocrylene, oxybenzone (EUSOLEX 4360), sulisobenzone, bisoctrizole (TINOSORB M), titanium dioxide, zinc oxide; carotenoids; free radical scavengers; spin traps; retinoids and retinoid precursors such as retinol, retinoic acid and retinyl palmitate; ceramides; polyunsaturated fatty acids; essential fatty acids; enzymes; enzyme inhibitors; minerals; hormones such as estrogens; steroids such as hydrocortisone; 2-dimethylaminoethanol; copper salts such as copper chloride; peptides containing copper, coenzyme Q10; amino acids such a proline; vitamins; lactobionic acid; acetyl-coenzyme A; niacin; riboflavin; thiamin; ribose; electron transporters such as NADH and FADH2; and other botanical extracts such as oat, aloe vera, Feverfew, Soy, Shiitake mushroom extracts, and derivatives and mixtures thereof.

In certain preferred embodiments, the compositions comprise a combination of *Pichia anomala* extract and n-acetyl glucosamine and at least one additional skin moisturizing active agent.

In certain preferred embodiments, the skin care compositions comprise the combination of *Pichia anomala* extract, n-acetyl glucosamine, and at least one additional agent for improving the appearance of at least one sign of aging in skin. Examples of suitable additional agents improving the appearance of at least one sign of aging in skin include, but are not limited to, tropoelastin promoters, collagen promoters, retinoids, hyaluronic acid including cross-linked hyaluronic acid, dimethylaminoethanol, N,N,N',N'-tetrakis (2-hydroxypropyl)ethylenediamine, alpha hydroxy acids, polyhydroxyacids, and combinations of two or more thereof.

"Tropoelastin promoters," as used herein, refers to a class of compounds that possess the biological activity of enhancing the production of tropoelastin. Tropoelastin promoters, according to the present invention, include all natural or synthetic compounds that are capable of enhancing the production of tropoelastin in the human body.

Examples of suitable tropoelastin promoters include, but are not limited to, blackberry extracts, cotinus extracts, feverfew extracts, and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof. In a preferred embodiment, the tropoelastin promoter is selected from blackberry extracts, cotinus extracts, feverfew extracts, and combinations thereof. In a particularly preferred embodiment, the tropoelastin promoter is selected from blackberry extracts, feverfew extracts, and combinations thereof.

By "blackberry extract," it is meant a blend of compounds isolated from the plant of the genus *Rubus*, and preferably *Rubus fruticosus*. In one embodiment, the compounds are isolated from the flowers of the plant. In a further embodiment, the compounds are isolated from dried flowers of the plant. Such compounds may be isolated from one or more part of the plant (e.g., the whole plant, flower, seed, root, rhizome, stem, fruit and/or leaf of the plant). In a preferred embodiment, the blackberry extract is a blackberry leaf extract. One particularly suitable blackberry extract is produced by extracting the leaves of *Rubus fruticosus* with a mixture of water and ethanol compounded to an activity of about 5% to about 10%, with a maltodextrin matrix, commercially available from Symrise Inc. of Teterboro, N.J., and is sold under the name SYMMATRIX.

Compositions of the present invention may include a cosmetically effective amount of one or more tropoelastin promoters such as those described above. The compositions preferably include, on an active basis, from about 0.1% to about 10% of the tropoelastin promoters, more preferably from about 0.5% to about 5% of tropoelastin promoters, and most preferably from about 0.5% to about 2% of the tropoelastin promoters.

"Collagen promoter," as used herein, refers to compounds that possess the biological activity of enhancing the production of collagen. "Non-retinoid collagen promoters" according to the present invention include all natural or synthetic compounds that are not retinoids, or derived from retinoids, and are capable of enhancing the production of collagen in the human body.

Examples of suitable collagen promoters include, but are not limited to the following: Retinoids including retinol, retinaldehyde, and retinoic acid, extracts of feverfew (*Tanacetum parthenium*), extracts of *Centella asiatica*, and extracts of *Siegesbeckia orientalis*; extracts of soy; collagen-promoting peptides; ursolic acid; and asiaticoside. *Centella asiatica*, also known as *Violette marronne* on Reunion Island, Gotu Kola or Indian pennywort in India, *Centella repanda* in North America, and Talapetraka in Madagascar, is a polymorphous herb and belongs to the family of Umbelliferae (Apiaceae), particularly to the Hydrocotyle subfamily. It grows wild throughout the tropics and prefers moist and shady regions at an altitude of about 600 to 1200 meters above sea level. *Centella asiatica* has three varieties: Typica, Abyssinica, and Floridana. The herb is known and used for its healing, sedative, analgesic, antidepressant, antiviral and antimicrobial properties. The biological activity of the herb appears to be due to the presence of triterpene molecules in the herb. A suitable extract of *Centella asiatica* is available as TECA from Bayer Consumer HealthCare of Basel, Switzerland.

By "extracts of *Siegesbeckia orientalis*," is meant any of various extracts of the plant *Siegesbeckia orientalis*, including Darutoside available from Sederma (Croda International Group of Edison, N.J.).

Suitable collagen-promoting peptides include the following matrikine peptides, (i.e., a peptide derived from the degradation of extracellular matrix proteins—collagen, elastin, or proteoglycan) including palmitoyl pentapeptides, such as MATRIXYL from Sederma (Croda International Group of Edison, N.J.); GHK copper peptide available as PROCYTE from Photomedex of Montgomeryville, Pa.; Palmitoyl GHK peptide available as Biopoeptide CL from Sederma (Croda International Group of Edison, N.J.); Biomimetic tetrapeptides, such as those available as Chronoline Tri Peptide from Unipex of Québec, Canada; and Palmitoyl tri-peptide, available as Syn-Coll from DSM of Basel, Switzerland.

Ursolic acid is also known as pentacyclic triterpene acid, Prunol, Malol, Urson, beta-ursolic acid and 3-Beta-Hydroxy-Urs-12-En-28-Oic Acid. It is commercially available for example from Sigma-Aldrich of St. Louis, Mo.

Asiaticoside, also known chemically as: [6-[[3,4-dihydroxy-6-(hydroxynnethyl)-5-(3,4,5-trihydroxy-6-methyloxan-2-yl)oxyoxan-2-yl]oxymethyl]-3,4,5-trihydroxyoxan-2-yl]10,11-dihydroxy-9-(hydroxynnethyl)-1,2,6a,6b,9,12a-hexamethyl-2,3,4,5,6,6a,7,8,8a,10,11,12,13,14b-tetradecahydro-1H-picene-4a-carboxylate) is commercially available for example from Bayer Sante Familiale Division Serdex, 69, Boulevard Victor Hugo 93400 SAINT-OUEN France.

Compositions of the present invention may include a cosmetically effective amount of one or more collagen promoters. The compositions preferably include, on an active basis, from about 0.1% to about 10% of the collagen promoters, more preferably from about 0.5% to about 5% of collagen promoters, and most preferably from about 0.5% to about 2% of the collagen promoters.

The compositions of the present invention may comprise additionally at least one skin lightening active agent. Examples of suitable skin lightening active agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs and silicas, zinc salts, and the like, and other agents as described in Solano et al. Pigment Cell Res. 19 (550-571) and Ando et al. Int J Mol Sci 11 (2566-2575).

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkylresorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliants include glycolic acid or salicylic acid.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, Portulaca extract, Licochalcone, chalcone, 2,2'-dihydroxy chalcone, Primula extract, propolis, and the like.

The additional cosmetically active agent may be present in a composition in any suitable amount, for example, in an amount of from about 0.0001% to about 20% by weight of the composition, e.g., about 0.001% to about 10% such as about 0.01% to about 5%. In certain preferred embodiments, in an amount of 0.1% to 5% and in other preferred embodiments from 1% to 2%.

Compositions of the present invention may include a cosmetically effective amount of one or more anti-inflammatory compounds.

Examples of suitable anti-inflammatory agents include substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts and materials derived from the following: *Phellodendron amurense* Cortex Extract (PCE), Non-Denatured Soy (Glycine max), Feverfew (*Tanacetum parthenium*), Ginger (*Zingiber officinale*), Ginko (*Ginkgo biloba*), Madecassoside (*Centella asiatica* extract ingredient), Cotinus (*Cotinus coggygria*), Butterbur Extract (*Petasites hybridus*), Goji Berry (*Lycium barbarum*), Milk Thistle Extract (*Silybum marianum*), Honeysuckle (*Lonicera japonica*), Basalm of Peru (*Myroxylon pereirae*), Sage (*Salvia officinalis*), Cranberry Extract (*Vaccinium oxycoccos*), Amaranth Oil (*Amaranthus cruentus*), Pomegranate (*Punica granatum*), Yerbe Mate (*Ilex paraguariensis* Leaf Extract), White Lily Flower Extract (*Lilium candidum*), Olive Leaf Extract (*Olea europaea*), Phloretin (apple extract), Oat Flour (*Aveena sativa*), Lifenol (Hops: *Humulus lupulus*) Extract, Bugrane P (*Ononis spinosa*), Licochalcone (Licorice: *Glycyrrhiza* inflate extract ingredient), Symrelief (Bisabolol and Ginger extract), combinations of two or more thereof, and the like.

In one embodiment, the anti-inflammatory agent is a resorcinol. Particularly suitable substituted resorcinols include 4-hexyl resorcinol and 4-octylresorcinol, particularly 4-hexyl resorcinol. 4-Hexyl resorcinol is commercially available as SYNOVEA HR from Sytheon of Lincoln Park, N.J. 4-Octylresorcinol is commercially available from City Chemical LLC of West Haven, Conn.

By "extracts of feverfew," it is meant extracts of the plant "*Tanacetum parthenium*," such as may be produced according to the details set for the in US Patent Application Publication No. 2007/0196523, entitled "PARTHENOLIDE FREE BIOACTIVE INGREDIENTS FROM FEVERFEW (*TANACETUM PARTHENIUM*) AND PROCESSES FOR THEIR PRODUCTION." One particularly suitable feverfew extract is commercially available as about 20% active feverfew, from Integrated Botanical Technologies of Ossining, N.Y.

In the skin care composition of the invention, the ratio of the amounts of the combined *Pichia anomala* extract and n-acetyl glucosamine to the anti-inflammatory compound may be varied. For example, the extract and the anti-inflammatory compound may be present in a weight ratio (which is determined by dividing the amount by weight of the dry extract by the amount by weight of the anti-inflammatory compound) of about 0.001 to about 100, preferably about 0.01 to about 10, more preferably about 0.25 to about 2.

A variety of other materials may also be present in the compositions of the present invention. In certain preferred embodiments, the composition comprises one or more topical ingredients selected from the group consisting of: surfactants, chelating agents, emollients, humectants, conditioners, preservatives, opacifiers, fragrances and the like.

What is meant by an emollient is a compound that helps to maintain the soft, smooth, and pliable appearance of the skin (e.g., by remaining on the skin surface or in the stratum corneum to act as a lubricant). Examples of suitable emollients include those found in Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.), and include, but are not limited to, petrolatum, hexyldecyl stearate and plant, nut, and vegetable oils such as macadamia nut oil, rice bran oil, grape seed oil, palm oil, prim rose oil, hydrogenates peanut oil, and avocado oil.

What is meant by a humectant is a compound intended to increase the water content of the top layers of skin (e.g., hygroscopic compounds). Examples of suitable humectants include those found Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.) and include, but are not limited to, glycerin, sorbitol or trehalose (e.g., α,α-trehalose, β, β-trehalose, α, β-trehalose) or a salt or ester thereof (e.g., trehalose 6-phosphate).

In one embodiment, the composition contains glycerin. For example, the composition contains at least about 4 wt % glycerin. The composition may contain at least about 10 wt % glycerin.

In another embodiment, the composition has a pH of about 6.5 or less. For example, the composition may have a pH of about 5.5 to about 6.

In a particular embodiment, the composition contains about 0.052 weight percent of an extract of *Pichia anomala* and about 2 weight percent of n-acetyl glucosamine.

The composition may further contain about 1 to about 2 weight percent of a mixture of cetearyl olivate and sorbitan olivate, about 4 to about 5 weight percent glycerin, and at least about 65 weight percent water, and have a pH of less than about 6.

What is meant by a surfactant is a surface-active agent intended to cleanse or emulsify. Examples of suitable surfactants include those found in Chapter 37, pages 431-450 (Classification of surfactants, by L. Oldenhove de Guertechin) in Handbook of Cosmetic Science and Technology (edited by A. Barel, M. Paye and H. Maibach, Published in 2001 by Marcel Dekker, Inc New York, N.Y.) and include, but are not limited to anionic surfactants such as sulfates, cationic surfactants such as betaines, amphoteric surfactants such as sodium coco glycinate, noionic surfactants such as alkyl polyglucosides.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the trade name VERSENE 100XL.

Suitable preservatives include, for example, parabens, quaternary ammonium species, phenoxyethanol, benzoates, DMDM hydantoin, organic acids and are present in the composition in an amount, based upon the total weight of the composition, from about 0 to about 1 percent or from about 0.05 percent to about 0.5 percent.

Any of a variety of conditioners which impart additional attributes, such as gloss to the hair, are suitable for use in this invention. Examples include, but are not limited to, volatile silicone conditioning agent having an atmospheric pressure boiling point less than about 220° C. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids. Other suitable conditioners include cationic polymers, including polyquarterniums, cationic guar, and the like.

Any of a variety of commercially available pearlescent or opacifying agents are suitable for use in the composition. Examples of suitable pearlescent or opacifying agents include, but are not limited to, mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: $HO-(JO)_a-H$, wherein J is an alkylene group having from about 2 to about 3 carbon atoms; and a is 2 or 3; fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof.

Any fragrance compositions suitable for use on skin may be used in accord with the present invention.

In certain preferred embodiments, the present invention is in the form of a substrate comprising a composition of the present invention. Any suitable substrate may be used. Examples of suitable substrates and substrate materials are disclosed, for example, in U.S. Published Application Nos. 2005/0226834 and 2009/0241242 which are incorporated herein by reference in their entirety.

In certain preferred embodiments, the substrate is a wipe, glove, or a facial mask. Preferably, such embodiments comprise a water-insoluble substrate as such is defined in the cited references above. For certain embodiments, the water-insoluble substrate may have a size and shape such that it covers the face of a human user to facilitate placing the water-insoluble substrate about the face of the user as a mask substrate. For example, the water-insoluble mask substrate may have openings for a mouth, nose, and/or eyes of the user. Alternatively, the water-insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval. For certain embodiments, the substrate is a glove such as described in U.S. Published Application No 2006/0141014 which is incorporated herein in its entirety. In one embodiment of the invention, the product includes a plurality of water-insoluble substrates of different shapes.

The present invention further comprises a method of improving the barrier function and moisturization of skin by applying to skin in need of improving skin barrier function and moisturization an extract of *Pichia anomala* and n-acetyl glucosamine. The method comprises for example topically applying a composition of the present invention comprising combined *Pichia anomala* extract and n-acetyl glucosamine to skin in need of improving skin barrier function and moisturization. Such topical application may be to any skin in need of treatment on the body, for example skin of the face, lips, neck, chest, back, arms, axilla, hands, feet and/or legs. The combined *Pichia anomala* extract and n-acetyl glucosamine are preferably applied in an effective amount that results in the desired improvement of skin barrier function being achieved.

The present invention further comprises a method of improving the appearance of at least one sign of skin aging by applying to skin in need of improving the appearance of at least one sign of skin aging combined *Pichia anomala* extract and n-acetyl glucosamine. The method comprises for example topically applying a composition of the present invention comprising combined *Pichia anomala* extract and n-acetyl glucosamine to skin in need of treatment of at least one sign of skin aging. Such topical application may be to any skin in need of treatment on the body, for example skin of the face, lips, neck, chest, back, arms, axilla, hands, feet and/or legs. The combined *Pichia anomala* extract and n-acetyl glucosamine are preferably applied in an effective amount that results in the desired improvement in the appearance of at least one sign of skin aging being achieved.

Any suitable method of applying the composition to the skin in need may be used. For example, the composition may be applied directly from a package to the skin in need, by hand to the skin in need, or may be transferred from a substrate such as a wipe or mask, or a combination of two or more thereof. In other embodiments, the composition may be applied via a dropper, tube, roller, spray, and patch or added to a bath or otherwise to water to be applied to the skin, and the like. The composition may be applied in a variety of manners/forms, including, without limitation, as a leave-on cream, mask, and/or serum.

In certain embodiments, the methods of the present invention comprise applying at least two different compositions or products comprising *Pichia anomala* extract and n-acetyl glucosamine to the skin. For example, the methods may comprise applying a first composition comprising an extract of *Pichia anomala*, followed by applying a second composition comprising n-acetyl glucosamine that is different from the first composition, to the skin in need of treatment.

In certain preferred embodiments, the first and second composition may be independently selected from the group consisting of lotions, cleansers, masks, wipes, creams, serums, gels, and the like. In certain preferred embodiments, at least one of the first and second compositions is a cleanser, lotion, cream, essence, or serum and the other is a facial mask or wipe. In certain other preferred embodiments, at least one of the first and second compositions is a cleanser and the other is a lotion or cream.

The composition and formulations and products containing such compositions of the present invention may be prepared using methodology that is well known by an artisan of ordinary skill. These compositions may be useful in treating skins of aging such as wrinkles, loss of elasticity, uneven skin including reducing blotchiness. The composition may be used on a routine basis and is substantially free of skin irritants.

In one embodiment, the invention provides a method of increasing the amount of hyaluronic acid produced by skin when contacted with an extract of *Pichia anomala*, comprising contacting the skin with a composition comprising the extract of *Pichia anomala* and n-acetyl glucosamine. In this manner, a low level of extract of *Pichia anomala*, for example less than about 0.1, or less than about 0.08, for example about 0.052, weight percent, may be used and still achieve good HA production. N-acetyl glucosamine may act as an activity booster for the extract of *Pichia anomala* in inducing HA production by skin.

The following non-limiting examples further illustrate the present invention.

Example 1

Hyaluronic acid (HA) production by human skin explants was determined after treating them with test Compositions 1-4 containing different amounts of *Pichia anomala* extract as follows.

First, a gel was made containing the ingredients set forth in Table 1.

TABLE 1

| INCI | Weight % |
| --- | --- |
| Phenoxyethanol; Methylparaben; Ethylparaben; Propylparaben | 0.7 |
| Carbomer | 1 |
| 20% Sodium Hydroxide Solution | QS (pH = 6) |
| Water | 98.3 |

Compositions 1-4 were made by combining 2 wt % of the gel with different amounts of a 5% aqueous solution of *Pichia anomala* extract, along with additional ingredients. The *Pichia anomala* had been grown on kiwi plant. The 5% aqueous solution was treated as a 100% stock solution.

Compositions 1-4 contained the ingredients shown in Table 2.

HA production by Compositions 1-4 was determined using immunohistology on normal explants of human skin from three donors (29, 30, 55 years old). Eight mm diameter punches were cut from the explants and deposited on pieces of sterile gauze and placed, one explant per well, in six well plates with 3 mL of culture media. The culture media was sold under the tradename GIBCO DMEM/F-12 (ThermoFisher Scientific, Waltham, Mass., catalog #11514436) with 1% GIBCO Penicillin-Streptomycin (ThermoFisher Scientific, catalog #11528876) and 0.1% amphotericin B sold under the tradename FUNGIZONE (ThermoFisher Scientific, catalog #11510496).

For each test composition, 5 µl of test composition was applied to an explant once a day for 5 days. An untreated explant sample was used as the control. On day 7 the explants were recovered, wiped with a sterile gauze, then cut in half vertically and fixed in 4% paraformaldehyde (V/V). On day 8 the explants were dehydrated and embedded in paraffin. Each test composition was tested in triplicate.

The paraffinized slides were stripped with xylene and epitope retrieval was carried out with PT link (Agilent, Santa Clara, Calif.) and target retrieval solution sold under the tradename ENVISION Flex, High pH (Dako, DM828, Agilent, Santa Clara, Calif.). Slides were then rinsed with wash buffer sold under the tradename ENVISION (Dako, DM831, Agilent, Santa Clara, Calif.) one time for 10 mins. Permeabilization and saturation were done with PBS 0.3% Triton/ 5% goat serum (Dako, Santa Clara, Calif., catalog #CP3418/ X090710-8) for 30 mins, followed by labeling with Hyaluronic Acid Binding Protein ("HABP" from Calbiochem, catalog #385911, Millipore Sigma, St. Louis, N.J.) overnight at 4° C. The next day the slides were rinsed with PBS three times for 5 minutes each. Antibody was revealed with biotin-binding protein covalently attached to a fluorescent label sold under the tradename ALEXA FLUOR 488 streptavidin (Invitrogen™ catalog #S11223) and staining of nuclei was done with DAPI solution (Dako, Santa Clara, Calif.) at 5 µg/ml for 30 min at ambient temperature. Slides were then rinsed with PBS and mounted with Fluoprep mounting medium (bioMerieux UK Ltd., UK catalog #75521).

Pictures of the skin sections were taken with an Olympus IX70 Fluorescence microscope (Olympus Corporation, Japan) coupled to an image analysis system (NIS-Elements AR software, Nikon Instruments, Melville, N.Y.). Quantitative analysis of images was conducted with ImageJ software.

The results are shown in Table 3. The results are expressed as average fluorescence intensity of the dermis (in

TABLE 2

| INCI | Composition 1 (weight %) | Composition 2 (weight %) | Composition 3 (weight %) | Composition 4 (weight %) |
| --- | --- | --- | --- | --- |
| Gel | 2 | 2 | 2 | 2 |
| Cetearyl Alcohol; Cetearyl Glucoside | 7 | 7 | 7 | 7 |
| Isononyl Isononanoate | 8 | 8 | 8 | 8 |
| Phenoxyethanol; Methylparaben; Ethylparaben; Propylparaben | 0.7 | 0.7 | 0.7 | 0.7 |
| 5% Aq. Solution of *Pichia anomala* extract | 2.5 (0.065 wt % *Pichia anomala* extract) | 5 (0.13 wt % *Pichia anomala* extract) | 7.5 (0.195 wt % *Pichia anomala* extract) | 10 (0.26 wt % *Pichia anomala* extract) |
| Water | 79.8 | 77.3 | 74.8 | 72.3 |

Arbitrary Units (AU)). Fluorescence intensity (green) is proportional to the synthesis of hyaluronic acid.

TABLE 3

| | Weight % of 5% Solution of *Pichia anomala* extract | Weight % of *Pichia anomala* extract | Delta of HAPB as compared to untreated control |
|---|---|---|---|
| Composition 1 | 2.5 | 0.065 | 10.37 |
| Composition 2 | 5 | 0.13 | 17.73 |
| Composition 3 | 7.5 | 0.195 | 15.24 |
| Composition 4 | 10 | 0.26 | 15.41 |

These results suggest that maximum HA production by skin is obtained using about 0.13 wt % of the *Pichia anomala* extract. Above this amount, production of HA leveled off.

Example 2

Hyaluronic acid (HA) production by human skin explants was determined after treating them with Compositions 5-7 according to the invention containing *Pichia anomala* extract and n-acetyl glucosamine.

Compositions 5-7 contained the ingredients shown in Table 4.

TABLE 4

| Phase | INCI | Composition 5 (Weight %) | Composition 6 (Weight %) | Composition 7 (Weight %) |
|---|---|---|---|---|
| A | Water | 69.4 | 69.4 | 69.4 |
| A | Hydroxethyl Acrylate/Sodium Acryloyldimethyl Taurate Copolymer | 1.2 | 1.2 | 1.2 |
| B | Sclerotium Gum | 0.4 | 0.4 | 0.4 |
| B | Glycerin | 4.0 | 4.0 | 4.0 |
| C | Cetearyl Olivate, Sorbitan olivate | 1.5 | 1.5 | 1.5 |
| C | Chlorphenesin | 0.2 | 0.2 | 0.2 |
| D | Water | 15 | 9 | 9 |
| D | N-acetylglucosamine | 3.0 | 1.0 | 2.0 |
| D | Glycerin | 1 | 1 | 1 |
| D | Glyceryl dilaurate | 0.5 | 0.5 | 0.5 |
| D | Steareth-10 | 0.5 | 0.5 | 0.5 |
| E | Dimethicone; Dimethicone Crosspolymer | 2.5 | 2.5 | 2.5 |
| E | Dimethicone | 3.0 | 3.0 | 3.0 |
| E | Dimethicone; Dimethiconol | 2 | 2 | 2 |
| F | 5% Extract of *Pichia anomala* solution | 1 (0.026 wt % *Pichia anomala* extract) | 3 (0.078 wt % *Pichia anomala* extract) | 2 (0.052 wt % *Pichia anomala* extract) |
| F | Ethylhexylglycerin; Phenoxyethanol | 0.8 | 0.8 | 0.8 |
| G | 20% Citric acid Solution | QS pH = 5.5-6 | QS pH = 5.5-6 | QS pH = 5.5-6 |
| G | 20% Sodium Hydroxide Solution | QS pH = 5.5-6 | QS pH = 5.5-6 | QS pH = 5.5-6 |

The compositions were prepared in phases. Phase A was prepared by combining water and Hydroxethyl Acrylate/Sodium Acryloyldimethyl Taurate Copolymer in a kettle bell mixer with a propeller stirring and mixed until fully dispersed, smooth and uniform. Phase B was prepared by pre-mixing sclerotium gum and glycerin until uniform, then added to the main kettle and again mixed until smooth and uniform. The main kettle was then heated to 70-75° C. Next, for Phase C, using a Greerco high speed homogenizer the Chlorphensin, Cetearyl Olivate, and Sorbitan olivate were added to the main kettle and mixed until a smooth, uniform bulk was formed. The main kettle was then cooled down to 60° C. with sweep blade mixing. Phase D was prepared by combining the water and n-acetyl glucosamine in a separate kettle while heating to 65° C., then the glycerin, glycerin dilaurate, and steareth-10 were added, mixed until uniform and held at 65° C. Once Phase D was uniform, it was added to the main kettle at 65° C. and mixed until uniform with sweep mixing. The mixture was then cooled to 40° C. In a second side kettle, Phase E was prepared by combining Dimethicone/Dimethicone Crosspolymer and Dimethicone, mixed until uniform, and then added to the main kettle at 40° C., followed by the addition of Dimethicone/Dimethiconol. In Phase F, the extract of *Pichia anomala* solution, ethylhexylglycerin, and phenoxyethanol were added to the main kettle at 40° C. or less and mixed until uniform. Lastly, the main kettle was cooled to 30° C. The pH was adjusted to 5.5-6 using 20% citric acid and/or 20% sodium hydroxide if needed (Phase G).

The compositions were evaluated according to the skin explant model described in Example 1 for change in HAPB production against untreated control. The results are shown in Table 5.

TABLE 5

| | Weight % of Pichia anomala extract | Weight % N-Acetyl Glucosamine | Delta of HAPB as compared to untreated control |
|---|---|---|---|
| Composition 5 | ---0.026--- | 3 | 14.35 |
| Composition 6 | --0.078--- | 1 | 12.34 |
| Composition 7 | ---0.052-- | 2 | 16.15 |

Although each of Compositions 5-7 contained 0.078 wt % or less of *Pichia anomala* extract, they all stimulated HA production in the explants at high levels in the presence of n-acetyl glucosamine. Composition 7 provided particularly good results. Composition 7 contained only 0.052 wt % *Pichia anomala* extract with 2 wt % n-acetyl glucosamine but provided a delta of HABP over untreated of 16.15, which is unexpectedly greater than the delta of HABP over untreated provided by Composition 1 in Example 1 (10.37) containing about the same amount of *Pichia anomala* extract (0.065 wt %).

We claim:

1. A topical composition comprising (i) less than about 0.1 weight percent of an extract of *Pichia anomala* and (ii) n-acetyl glucosamine.

2. The topical composition of claim 1, wherein the extract of *Pichia anomala* is prepared from a strain of *Pichia anomala* present on kiwi fruit or leaves.

3. The topical composition of claim 1, wherein the extract of *Pichia anomala* is prepared from a strain of *Pichia anomala* present on sugar cane.

4. The topical composition of claim 1, wherein the weight ratio of the extract of *Pichia anomala* to n-acetyl glucosamine in the topical composition is about 0.026.

5. The topical composition of claim 1 further comprising at least 4 weight percent glycerin.

6. The topical composition of claim 1 having a pH of about 6.5 or less.

7. A topical composition comprising about 0.052 weight percent of an extract of *Pichia anomala* and about 2 weight percent of n-acetyl glucosamine.

8. The topical composition of claim 7 further comprising about 1 to about 2 weight percent of a mixture of cetearyl olivate and sorbitan olivate, about 4 to about 5 weight percent glycerin, and at least about 65 weight percent water, and having a pH of less than about 6.

9. A method of treating a sign of skin aging, comprising topically applying to skin in need of treatment for skin aging a topical composition comprising (i) less than about 0.1 weight percent of an extract of *Pichia anomala* and (ii) n-acetyl glucosamine.

10. A method of improving skin barrier function and moisturization, comprising topically applying to skin in need of improving skin barrier function and moisturization a topical composition comprising (i) less than about 0.1 weight percent of an extract of *Pichia anomala* and (ii) n-acetyl glucosamine.

11. A method of increasing the amount of hyaluronic acid produced by skin when contacted with an extract of *Pichia anomala*, comprising contacting the skin with a composition comprising (i) less than about 0.1 weight percent of an extract of *Pichia anomala* and (ii) n-acetyl glucosamine.

12. The method of claim 11, wherein the composition contains about 0.052 weight percent of the extract of *Pichia anomala* and about 2 weight percent of n-acetyl glucosamine.

13. The method 12, wherein the composition further comprises about 1 to about 2 weight percent of a mixture of cetearyl olivate and sorbitan olivate, about 4 to about 5 weight percent glycerin, and at least about 65 weight percent water, and has a pH of less than about 6.

* * * * *